United States Patent [19]

Voorhees

[11] 4,211,770
[45] Jul. 8, 1980

[54] TREATMENT OF PSORIASIS INTRALESIONALLY WITH $N^6$-2'-O-DIBUTYRYL CYCLIC AMP

[75] Inventor: John J. Voorhees, Ann Arbor, Mich.

[73] Assignee: The Upjohn Company, Kalamazoo, Mich.

[21] Appl. No.: 629,914

[22] Filed: Nov. 7, 1975

Related U.S. Application Data

[63] Continuation of Ser. No. 425,340, Dec. 17, 1973, abandoned, which is a continuation-in-part of Ser. No. 324,012, Jan. 16, 1973, abandoned.

[51] Int. Cl.$^2$ .................. A61K 31/70; A61K 31/705
[52] U.S. Cl. .................................. 424/180; 424/182; 424/361
[58] Field of Search .................. 424/180; 260/211.5 R

[56] References Cited

U.S. PATENT DOCUMENTS 3,849,553  11/1974  Dea et al. .................. 424/180

FOREIGN PATENT DOCUMENTS 2077725  5/1971  France .................. 424/200

OTHER PUBLICATIONS

Lapinet et al., Chem. Abst., vol. 80 (1974), p. 112,625r.

*Primary Examiner*—Anna P. Fagelson
*Attorney, Agent, or Firm*—John J. Killinger

[57] ABSTRACT

Pharmaceutical composition for treatment of proliferating skin diseases, primarily psoriasis. The compositions comprise a pharmaceutical carrier with a compound of the formula

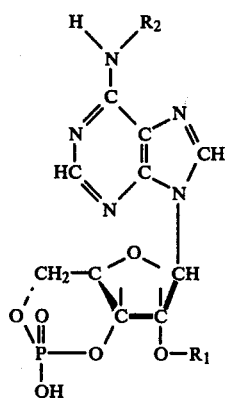

Formula 1 wherein $R_1$ and $R_2$ are the same or different and selected from the group consisting of benzoyl, adamantane carboxylate or an acyl radical of an aliphatic carboxylic acid having from 2 to 18 carbon atoms inclusive including the pharmacologically acceptable acid addition salts thereof as the active compound.

The compositions are administered to humans and animals systemically or topically.

1 Claim, No Drawings

TREATMENT OF PSORIASIS INTRALESIONALLY WITH N⁶-2'-O-DIBUTYRYL CYCLIC AMP

CROSS-REFERENCE TO RELATED APPLICATION

This application is a continuation of application Ser. No. 425,340, filed Dec. 17, 1973, now abandoned, which is a continuation-in-part of prior application Ser. No. 324,012, filed Jan. 16, 1973, now abandoned for "Pharmaceutical Composition and Process of Treatment".

BRIEF DESCRIPTION OF THE INVENTION

This invention relates to pharmaceutical compositions for application to the skin and to a method for the treatment of proliferating skin diseases. The compositions may be applied topically, or by injection such that the composition enters the blood stream or intralesionally, intradermally, or sub-cutaneously or orally. The treatment can be either therapeutic or prophylactic.

DETAILED DESCRIPTION OF THE INVENTION

Proliferative skin diseases are widespread throughout the world and afflict millions of humans and their domesticated animals. This invention provides a method for treatment of such diseases and pharmaceutical compositions which are useful in alleviating them. As used hereinafter in this specification and in the claims, the expression "proliferative skin diseases" means benign and malignant proliferative skin diseases which are characterized by accelerated cell division in the epidermis, dermis or appendages thereto, associated with incomplete tissue differentiation. Such diseases include: psoriasis, atopic dermatitis, non-specific dermatitis, primary irritant contact dermatitis, allergic contact dermatitis, basal and squamous cell carcinomas of the skin, lamellar ichthyosis, epidermolytic hyperkeratosis, premalignant sun induced keratosis, non-malignant keratosis, acne, and seborrheic dermatitis in humans and atopic dermatitis and mange in domesticated animals.

Heretofore, proliferative skin diseases have been generally accepted by mankind as an ongoing evil having degrees of severity variable with time, with inherited skin traits and external factors but always have been recognized as unsightly, painful, morbid diseases. Over the history of mankind innumerable medicines and treatments have been proposed, tried and used with varying degrees of success. However, no treatment heretofore devised or pharmaceutical composition used has been entirely successful in the wide spectrum of specific diseases encompassed by the expression proliferative skin diseases.

The present day treatments of a commercial nature which are prescribed and used for the treatment of proliferative skin diseases include three approaches: (1) topical applications: coal tar derivatives, 5 fluorouracil, vitamin A acid, glucocorticoids in high dosage (constituting a non-permissive concentration), bath oils and non-specific emollient creams and ointments; (2) the systemic administration: glucocorticoids and classic anti-cancer agents, for example, methothrexate, hydroxyurea, azaribine, cyclophosphamide; (3) physical modalities: ultra voilet light, x-irradiation, and in severe cases, surgery.

While these treatments provide, in certain cases, some remission of the original symptoms, each treatment suffers some defect, for example, temporary and incomplete mitigation of symptoms, rapid re-occurrence of the disease when mitigation is terminated, serious and sometimes irreversible damage (atrophy) resulting from the topical application for extended times of glucocorticoids, acute bone marrow suppression and cirrhosis of the liver resulting from the protracted use of methothrexate which may lead to death of the patient, and the causation of cancer by the application of anti-cancer drugs, x-irradiation, or ultra violet rays.

In accordance with this invention it has been found that proliferative skin diseases are alleviated, that is, the symptoms of the disease are noticeably improved or become undetectable, by the treatment of the afflicted patient, or animal, with one or more of the pharmaceutical compositions described in detail hereinbelow.

For the purposes of this specification and the claims, a proliferative skin disease is alleviated when there is a noticeable decrease in the thickness of a lesion to palpation, with or without residual redness, or residual slightly dilated blood vessels or residual hyper- or hypo- pigmentation. For purposes of this invention and the claims hereof, psoriasis is alleviated when a scale-free psoriasis lesion is noticeably decreased in thickness, or noticeably but incompletely cleared or completely cleared.

The compositions may be applied topically or by injection such that the composition enters the blood stream, or intradermally, intra- or peri-lesionally, or sub-cutaneously.

The term "topical" as employed herein relates to the use of the active ingredient incorporated in a suitable pharmaceutical carrier, and applied at the site of the disease for exertion of local action. Accordingly, such topical compositions include those pharmaceutical forms in which the compound is applied externally by direct contact with the skin surface to be treated. Conventional pharmaceutical forms for this purpose include ointments, lotions, pastes, jellies, sprays, aerosols, bath oils and the like. The term "ointment" embraces formulations (including creams) having oleaginous, absorption, water-soluble and emulsion-type bases, e.g., petrolatum, lanolin, polyethylene glycols, as well as mixtures thereof. It has been found that topical application with occlusion of an area larger than the medicated area produces improved results relative to non-occluded topical application and is, therefore, the preferred method of topical treatment with the compositions of this invention.

Injection "intradermally" refers to positioning the composition in the high dermis by needle injection, or by high pressure air injection.

Injection "intra- or peri-lesionally" refers to positioning the composition into the lesion or into the tissue adjacent to the lesion.

The compositions may be injected so as to reach the blood stream intramuscularly, subcutaneously, rectally by suppositories, sublingually, intravenously, orally, by inhalation, or by application to non-diseased skin.

Examples of aliphatic carboxylic acids providing the acyl moiety are the saturated and unsaturated, straight or branched chain aliphatic carboxylic acids, for example, acetic, propionic, butyric, isobutyric, tert-butylacetic, valeric, isovaleric, caproic, caprylic, decanoic, dodecanoic, lauric, tridecoic, myristic, pentadecanoic, palmitic, margaric, stearic, undecylenic, oleic, hexynoic, heptynoic, and octynoic acids and the like.

The compositions of the present invention are presented for systemic administration to humans and animals in unit dosage forms, such as tablets, capsules, pills, powders, granules, sterile parenteral solutions or suspensions, and oral solutions or suspensions, and oil-water emulsions containing suitable quantities of a compound of formula 1 or its pharmacologically acceptable salts.

For oral administration either solid or fluid unit dosage forms can be prepared. For preparing solid compositions such as tablets, the principal active ingredient is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. The tablets can be laminated or otherwise compounded to provide a dosage form affording the advantage of prolonged or delayed action or predetermined successive action of the enclosed medication. For example, the tablet can comprise an inner dosage and an outer dosage component, the latter being in the form of an envelope over the former.

Alternatively, the two component system can be utilized for preparing tablets containing two or more incompatible active ingredients. Wafers are prepared in the same manner as tablets, differing only in shape and the inclusion of sucrose or other sweetener and flavor. In their simplest embodiment, capsules, like tablets, are prepared by mixing the active compound with an inert pharmaceutical diluent and filling the mixture into a hard gelatin capsule of appropriate size. In another embodiment, capsules are prepared by filling hard gelatin capsules with polymeric acid coated beads containing the active compound. Soft gelatin capsules are prepared by machine encapsulation of a slurry of the active compound with an acceptable vegetable oil, light liquid petrolatum or other inert oil.

Fluid unit dosage forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using a hydro-alcoholic (ethanol) vehicle with suitable sweeteners such as sugar and saccharin, together with an aromatic flavoring agent.

Suspensions can be prepared of the insoluble forms with a syrup vehicle with the aid of a suspending agent such as acacia, tragacanth, methylcellulose and the like.

Topical ointments can be prepared by dispersins the active compound in a suitable ointment base such as petrolatum, lanolin, polyethylene glycols, mixtures thereof, and the like. Advantageously, the compound is finely divided by means of a colloid mill utilizing light liquid petrolatum as a levigating agent prior to dispersing in the ointment base. Topical creams and lotions are prepared by dispersing the compound in the oil phase prior to the emulsification of the oil phase in water.

For parenteral administration, fluid unit dosage forms are prepared utilizing the active compound and a sterile vehicle, water being preferred. The compound, depending on the form and concentration used, can be either suspended or dissolved in the vehicle. In preparing solutions, a water-soluble form of the compound can be dissolved in water for injection and filter sterilized before filling into a suitable vial or ampule and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution.

The term unit dosage form as used in the specification and claims refers to physically discrete units suitable as unitary dosages for human subjects and animals, each unit containing a predetermined quantity of active material calculated to produce the desired therapeutic effect in association with the required pharmaceutical diluent, carrier or vehicle. The specifications for the novel unit dosage forms of this invention are dictated by and directly dependent on (a) the unique characteristics of the active material and the particular therapeutic effect to be achieved, and (b) the limitations inherent in the art of compounding such an active material for therapeutic use in humans and animals, as disclosed in detail in this specification, these being features of the present invention. Examples of suitable unit dosage forms in accord with this invention are tablets, capsules, pills, troches, suppositories, powder packets, granules, wafers, cachets, teaspoonfulls, tablespoonfuls, dropperfuls, ampules, vials, segregated multiples of any of the foregoing, and other forms as herein described.

The dosage of a compound of formula 1 for systemic treatment depends on route of administration; the age, weight, and condition of the patient; and the particular disease to be treated. A dosage schedule of from about 5 to 500 mg., 1 to 4 times daily (every six hours), embraces the effective range for the treatment of most conditions for which the compositions are effective.

A compound of the formula 1 is compounded with a suitable pharmaceutical carrier in unit dosage form for convenient and effective administration. In the preferred embodiments of this invention, the dosage units contain a compound of formula 1 in: 5, 75, 100 and 500 mg. amounts for systemic treatment; in 0.1, 0.5, 1, 5 and 15% amounts for topical or localized treatment; and 0.1 to 15% w/v for parenteral treatment. The dosage of compositions containing a compound of formula 1 and one or more other active ingredients is to be determined with reference to the usual dosage of each such ingredient.

The compositions of this invention may be employed in conjunction with glucocorticoids. The expression "glucocorticoids" refers to a naturally occurring product of the adrenal cortex, or a synthetic analog possessing anti-inflammatory activity and minimal or no mineralocorticoid activity or sex steroid activity. Of the natural glucocorticoids, one may use for example, hydrocortisone or the synthetic glucocorticoids such as methyl prednisolone acetate (Prednisone) for oral application or triamcinolone for topical therapy. The glucocorticoids should be employed in minor amounts or "permissive dosage". The expression "permissive dosage" for glucocorticoids refers to a quantity which minimally supplements the natural output of adrenal cortical glucocorticoids in a normal person and which dosage administered, alone, has no perceptible effect on proliferative skin diseases.

The following examples are illustrative of the best mode contemplated by the inventors for carrying out their invention and are not to be construed as limiting.

EXAMPLE 1

Capsules

One thousand two-piece hard gelatin capsules for oral use, each containing 200 mg. of $N^6$-2'-O-dibutyryl cyclic AMP are prepared from the following types and amounts of materials:

| | |
|---|---|
| $N^6$-2'-O-dibutyryl cyclic AMP | 200 gm. |
| Corn starch | 150 gm. |
| Talc | 75 gm. |
| Magnesium stearate | 2.5 gm. |

The materials are thoroughly mixed and then encapsulated in the usual manner.

The foregoing capsules are useful for the systemic treatment of psoriasis in adult humans by the oral administration of 1 capsule every 4 hours.

Using the procedure above, capsules are similarly prepared containing in 5, 100, and 500 mg. amounts by substituting 5, 100 and 500 gm. of $N^6$-2'-O-dibutyryl cyclic AMP for the 200 gm. used above.

EXAMPLE 2

Capsules

One thousand two-piece hard gelatin capsules for oral use, each containing 200 mg. of $N^6$-2'-O-dibutyryl cyclic AMP are prepared from the following types and amounts of ingredients:

| | |
|---|---|
| $N^6$-2'-O-dibutyryl cyclic AMP | 200 gm. |
| Corn starch | 250 gm. |
| Talc | 75 gm. |
| Magnesium stearate | 2.5 gm. |

The ingredients are thoroughly mixed and then encapsulated in the usual manner.

The foregoing capsules are useful for the systemic treatment of psoriasis in adult humans by the oral administration of 1 capsule every 6 hours.

EXAMPLE 3

Tablets

One thousand tablets for oral use, each containing 500 mg. of $N^6$-2'-O-dibutyryl cyclic AMP are prepared from the following types and amounts of materials:

| | |
|---|---|
| $N^6$-2'-O-dibutyryl cyclic AMP | 500 gm. |
| Lactose | 125 gm. |
| Corn starch | 65 gm. |
| Magnesium stearate | 7.5 gm. |
| Light liquid petrolatum | 3 gm. |

The ingredients are thoroughly mixed and slugged. The slugs are broken down by forcing through a number sixteen screen. The resulting granules are then compressed into tablets, each tablet containing $N^6$-2'-O-dibutyryl cyclic AMP.

The foregoing tablets are useful for systemic treatment of psoriasis in adult humans by oral administration of 1 tablet every 4 hours.

EXAMPLE 4

Oral syrup

One thousand cc. of an aqueous suspension for oral use, containing in each 5 cc. dose 200 mg. of $N^6$-2'-O-dibutyryl cyclic AMP is prepared from the following types and amounts of ingredients:

| | |
|---|---|
| $N^6$-2'-O-dibutyryl cyclic AMP | 40 gm. |
| Citric acid | 2 gm. |
| Benzoic acid | 1 gm. |
| Sucrose | 700 gm. |
| Tragacanth | 5 gm. |
| Lemon oil | 2 cc. |
| Deionized water q.s. | 1000 cc. |

The citric acid, benzoic acid, sucrose, tragacanth, and lemon oil are dispersed in sufficient water to make 850 cc. of solution. The $N^6$-2'-O-dibutyryl cyclic AMP, finely powdered, are stirred into the syrup until uniformly distributed. Sufficient water is added to make 1000 cc.

The composition so prepared is useful in the systemic treatment of psoriasis in adult humans at a dose of 1 teaspoonful 4 times a day.

EXAMPLE 5

Parenteral solution

A sterile aqueous solution for intramuscular use, containing in 1 cc. 75 mg. of $N^6$-2'-O-dibutyryl cyclic AMP is prepared from the following types and amounts of materials:

| | |
|---|---|
| $N^6$-2'-O-dibutyryl cyclic AMP | 75 gm. |
| Lidocaine hydrochloride | 4 gm. |
| Methylparaben | 2.5 gm. |
| Propylparaben | 0.17 gm. |
| Water for injection q.s. | 1000 cc. |

The ingredients are dissolved in the water and the solution sterilized by filtration. The sterile solution is filled into vials and the vials sealed.

The composition is useful in the systemic treatment of psoriasis at a dose of 1 cc. 4 times a day.

EXAMPLE 6

Parenteral solution

A sterile aqueous solution for intradermal use, containing in 1 cc. 5 mg. of $N^6$-2'-O-dibutyryl cyclic AMP is prepared from the following types and amounts of ingredients:

| | |
|---|---|
| $N^6$-2'-O-dibutyryl cyclic AMP | 5 gm. |
| Sodium chloride 10% Solution q.s. | |
| Water for injection q.s. | 1000 cc. |

The $N^6$-2'-O-dibutyryl cyclic AMP is added to the water and sufficient sodium chloride added to form an isotonic solution and the solution sterilized by filtration.

The sterile solution is administered intradermally by high pressure injection for treatment of psoriasis.

EXAMPLE 7

Topical ointment

One thousand gm. of 0.25% ointment is prepared from the following types and amounts of ingredients:

| | |
|---|---|
| $N^6$-2'-O-dibutyryl cyclic AMP | 2.5 gm. |
| Liquid petrolatum (heavy) | 250 gm. |
| Wool fat | 200 gm. |
| White petrolatum q.s. | 1000 gm. |

The white petrolatum and wool fat are melted and 100 gm. of liquid petrolatum added thereto. The $N^6$-2'-O-dibutyryl cyclic AMP are added to the remaining liquid petrolatum and the mixture milled until the powder is finely divided and uniformly dispersed. The powder mixture is stirred into the white petrolatum mixture and stirring continued until the ointment congeals.

The foregoing ointment is usefully applied topically to the skin of animals for the treatment of mange.

EXAMPLE 8

Cream

One thousand gm. of a topical cream are prepared from the following types and amounts of ingredients:

| | |
|---|---|
| $N^6$-2'-O-dibutyryl cyclic AMP | 50 gm. |
| Tegacid Regular* | 150 gm. |
| Spermaceti | 100 gm. |
| Propylene glycol | 50 gm. |
| Polysorbate 80 | 5 gm. |
| Methylparaben | 1 gm. |
| Deionized water q.s. | 1000 gm. |

*Self-emulsifying glyceryl monostearate from Goldschmidt Chemical Corporation, New York, N.Y.

The Tegacid and spermaceti are melted together at a temperature of 70°–80° C. The methylparaben is dissolved in about 500 mg. of water and the propylene glycol, polysorbate 80, and $N^6$-2'-O-dibutyryl cyclic AMP are added in turn, maintaining a temperature of 75°–80° C. The methylparaben mixture is added slowly to the Tegacid and spermaceti melt, with constant stirring. The addition is continued for at least 30 minutes with continued stirring until the temperature has dropped to 40°–45° C. The pH of the final cream is adjusted to 3.5 by incorporation 2.5 gm. of citric acid and 0.2 gm. of dibasic sodium phosphate dissolved in about 50 gm. of water. Finally, sufficient water is added to bring the final weight to 1000 gm. and the preparation stirred to maintain homogeneity until cooled and congealed.

The foregoing composition is useful for the treatment of psoriasis by applying to the lesions with occlusive bandage.

EXAMPLE 9

Following the procedure of the preceding Examples 1 to 8, inclusive, substituting an equal amount each of 2'-O-Monoacetyl cyclic AMP, $N^6$-Monoacetyl cyclic AMP, $N^6$-2'-O-Diacetyl cyclic AMP 2'-O-Monobutyryl cyclic AMP, $N^6$-Monobutyryl cyclic AMP, $N^6$-Monohexanoyl cyclic AMP, $N^6$-2'-O-Dihexanoyl cyclic AMP, 2'-O-Monooctanoyl cyclic AMP, $N^6$-Monooctanoyl cyclic AMP, $N^6$-2,-O-Dioctanoyl cyclic AMP, $N^6$-Monolauryl cyclic AMP, $N^6$-Monostearyl cyclic AMP, $N^6$-Monobenzoyl cyclic AMP, $N^6$-Monoadamantane carboxylate cyclic AMP, Ethyl ester cyclic AMP for the $N^6$-2'-O-dibutyryl cyclic AMP, compositions are prepared which are useful for the treatment of psoriasis.

EXAMPLE 10

The compositions prepared in the preceeding examples 1 through 9, inclusive, can similarly be administered for treatment of atopic dermatitis, non-specific dermatitis, primary irritant contact dermatitis, allergic contact dermatitis, basal and squamous cell carcinomas of the skin, lamellar ichthyosis, epidermolytic hyperkeratosis, premalignant sun induced keratosis, non-malignant keratosis, acne, and seborrheic dermatitis in humans and atopic dermatitis and mange in domesticated animals.

I claim:

1. A method for treating psoriasis in humans comprising the administration to a human suffering from psoriasis of an effective dose for treating psoriasis of $N^6$-2'-O-dibutyryl cyclic AMP in a suitable pharmaceutical carrier wherein the administration is to the psoriatic lesion intralesionally.

* * * * *